United States Patent
Osman et al.

(10) Patent No.: US 12,073,634 B2
(45) Date of Patent: Aug. 27, 2024

(54) COCKPIT DISPLAY AMBIENT LIGHTING INFORMATION FOR IMPROVING GAZE ESTIMATION

(71) Applicant: Rockwell Collins, Inc., Cedar Rapids, IA (US)

(72) Inventors: Ahmad F. Osman, Wethersfield, CT (US); Peggy Wu, Ellicott City, MD (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 369 days.

(21) Appl. No.: 17/514,315

(22) Filed: Oct. 29, 2021

(65) Prior Publication Data

US 2023/0044247 A1  Feb. 9, 2023

Related U.S. Application Data

(60) Provisional application No. 63/230,297, filed on Aug. 6, 2021.

(51) Int. Cl.
*G06V 20/59* (2022.01)
*A61B 3/00* (2006.01)
(Continued)

(52) U.S. Cl.
CPC .......... *G06V 20/59* (2022.01); *A61B 3/0008* (2013.01); *A61B 3/112* (2013.01); *A61B 3/113* (2013.01);
(Continued)

(58) Field of Classification Search
CPC ....... A61B 3/0008; A61B 3/112; A61B 3/113; G06F 3/013; G06N 20/00
See application file for complete search history.

(56) References Cited

U.S. PATENT DOCUMENTS 4,894,777 A * 1/1990 Negishi .................. G06F 3/013
700/83
6,199,985 B1  3/2001 Anderson
(Continued)

FOREIGN PATENT DOCUMENTS

WO  WO-2017155826 A1 * 9/2017  ............. G06F 21/32
WO  2020219063 A1  10/2020

OTHER PUBLICATIONS

Ramsoy, Thomas Zoega et al., "Predictive Value of Body Posture and Pupil Dilation in Assessing Consumer Preference and Choice", CBS Copenhagen Business School, 2017, Uploaded to Research@CBS: Dec. 2018, 39 pages.

(Continued)

*Primary Examiner* — Nabil H Syed
*Assistant Examiner* — Cal J Eustaquio
(74) *Attorney, Agent, or Firm* — Suiter Swantz IP

(57) ABSTRACT

A computer-implemented method is described. The method is be implemented by processors of an aircraft system. The method includes receiving images of an eye and a lighting configuration associated with a cockpit of an aircraft. The method further includes detecting a position of the eye within each of the images. The method further includes compensating for a pupillary light response of the eye based on the position of the eye within the image and the lighting configuration. By compensating for the pupillary light response, a fatigue level of the operator is estimated with reduced noise.

15 Claims, 4 Drawing Sheets

(51) Int. Cl.
  *A61B 3/11* (2006.01)
  *A61B 3/113* (2006.01)
  *G06F 3/01* (2006.01)
  *G06N 20/00* (2019.01)
  *G06V 10/60* (2022.01)
  *G06V 40/19* (2022.01)

(52) U.S. Cl.
  CPC ............ *G06F 3/013* (2013.01); *G06N 20/00* (2019.01); *G06V 10/60* (2022.01); *G06V 40/19* (2022.01)

(56) References Cited

U.S. PATENT DOCUMENTS

| | | |
|---|---|---|
| 10,016,130 B2 | 7/2018 | Ganesan et al. |
| 10,614,586 B2 | 4/2020 | Benedetto |
| 10,682,048 B2 | 6/2020 | Karakaya et al. |
| 2014/0152792 A1* | 6/2014 | Krueger ............... A61B 5/4863 348/78 |
| 2016/0167672 A1* | 6/2016 | Krueger ................ G16H 40/63 340/576 |
| 2016/0227257 A1* | 8/2016 | Frishman ............... H04N 19/65 |
| 2018/0329999 A1* | 11/2018 | Kale .................... G06F 16/2455 |
| 2020/0207358 A1 | 7/2020 | Katz et al. |
| 2021/0000339 A1 | 1/2021 | Neice |

OTHER PUBLICATIONS

Hayes et al: "Mapping and correcting the influence of gaze position on pupil size measurements", Behavior Research Methods, Springer US, New York, vol. 48, No. 2, May 8, 2015 (May 8, 2015), pp. 510-527, XP035865172, DOI: 10.3758/SI3428-015-0588-X [retrieved on May 8, 2015].

Klingner: "Measuring Cognitive Load During Visual Tasks by Combining Pupillometry and Eye Tracking", May 31, 2010 (May 31, 2010), XP055256289, Retrieved from the Internet: URL:http://graphics.stanford.edu/papers/kl ingner-dissertation/klingner-dissertation. pdf [retrieved on Mar. 8, 2016].

Pfleging et al.: "A Model Relating Pupil Diameter to Mental Workload and Lighting Conditions", Human Factors in Computing Systems, ACM, 2 Penn Plaza, Suite 701 New York NY 10121-0701 USA, May 7, 2016 (May 7, 2016), pp. 5776-5788, XP058257205, DOI: 10.1145/2858036.2858117.

Pignoni Giovanni et al: "Accounting for Effects of Variation in Luminance in Pupillometry for Field Measurements of Cognitive Workload", IEEE Sensors Journal, IEEE, USA, vol. 21, No. 5, Nov. 16, 2020 (Nov. 16, 2020), pp. 6393-6400, XP011835606, ISSN: 1530-437X, DOI: 10.1109/JSEN.2020.3038291 [retrieved on Feb. 4, 2021].

Piotr et al.: "Modeling Human Pupil Dilation to Decouple the Pupillary Light Reflex", Open Physics, vol. 17, No. 1, Sep. 17, 2019 (Sep. 17, 2019), pp. 458-467, XP093007250, DOI: 10.1515/phys-2019-0047.

* cited by examiner

COCKPIT DISPLAY AMBIENT LIGHTING INFORMATION FOR IMPROVING GAZE ESTIMATION

CROSS REFERENCE TO RELATED APPLICATIONS

The present application claims the benefit under 35 U.S.C. Section 119(e) of U.S. Provisional Application No. 63/230,297, filed on Aug. 6, 2021, naming Ahmad Osman and Peggy Wu as inventors, titled COCKPIT DISPLAY AMBIENT LIGHTING INFORMATION FOR IMPROVING GAZE ESTIMATION, which is incorporated herein by reference in the entirety.

TECHNICAL FIELD

Embodiments of the present invention are directed generally toward to the field of pupillometry, and more particularly to estimating fatigue of an aircraft operator based on pupillometry.

BACKGROUND

An aircraft operator may experience fatigue impacting a capability or response time during flight. One method of determining aircraft operator fatigue is by self-report surveys. Such self-report surveys may not contain high objectivity and are not provided in real-time. Eye gaze and other eye metrics such as pupillometry have been found in controlled laboratory environments to predict fatigue and workload. However, in operational environments, the eye metrics may be overwhelmed due to a pupillary light reflex to lighting within the environment, thereby introducing noise to the fatigue detection process. The pupillary light reflex is an autonomic reflex within eyes in response to light. The pupillary light reflex causes the pupil of the eye to constrict or dilate in response to light. The pupil may dilate as the intensity of the light is decreased. Similarly, the pupil may contract as intensity of the light is decreased. Such contraction and dilation may allow the eye to selectively control the amount of light passing to the retina, even in circumstances where the operator is fatigued. Therefore, it would be advantageous to provide one or more of a device, system, or method that cures the shortcomings described above.

SUMMARY

A computer-implemented method is described, in accordance with one or more embodiments of the present disclosure. In one embodiment, the method includes receiving images and a lighting configuration. The images are taken by a camera during operation of an aircraft and the images. The images also correspond to the light reflected from an eye of an operator occupying a cockpit of the aircraft. Such light reflected from the eye is based on the lighting configuration. Such lighting configuration corresponds to multiple flight displays and one or more aircraft instruments. In another embodiment, the method includes determining a position of the eye for each of the images by applying an eye detection model to each of the images. In another embodiment, the method includes generating one or more light-compensated pupil metrics for each of the images by applying a light compensation model to each of the images. The light compensation model uses the position of the eye and the lighting configuration to correct for a pupillary light reflex of the eye when applied to each image.

An aircraft system is also described, in accordance with one or more embodiments of the present disclosure. In one embodiment, the aircraft system includes flight displays within a cockpit of an aircraft, the flight displays each generating one or more display images during operation of the aircraft. In another embodiment, the aircraft system includes one or more aircraft instruments within the cockpit. In another embodiment, the aircraft system includes a camera positioned and oriented within the cockpit such that the camera is configured to capture images. The images are taken by the camera during the operation of the aircraft and correspond to light reflected from an eye of an operator occupying the cockpit of the aircraft. The light reflected from the eye is based on a lighting configuration of the of flight displays and the one or more aircraft instruments. In another embodiment, the aircraft system includes a processor configured to execute program instructions maintained on a memory. In another embodiment, the program instructions cause the processor to receive the images and the lighting configuration. In another embodiment, the program instructions cause the processor to determine a position of the eye for each of the images by applying an eye detection model to each of the images. In another embodiment, the program instructions cause the processor to generate one or more light-compensated pupil metrics for each of the images by applying a light compensation model to each of the plurality of images. The light compensation model using the position of the eye and the lighting configuration to correct for a pupillary light reflex of the eye.

A method of generating a light compensation model is also described, in accordance with one or more embodiments of the present disclosure. In one embodiment, the method includes generating a simulation environment of an aircraft cockpit. The simulation environment is one of a physical simulation environment or a virtual simulation environment. In another embodiment, the method includes selectively controlling lighting within the simulation environment. In another embodiment, the method includes capturing images of an eye within the simulation environment. In another embodiment, the method includes, storing the lighting configuration and the associated images in a memory. The selective control, capturing images, and storing may then be iteratively performed to achieve a training dataset. In another embodiment, the method includes, generating a light compensation model using the stored lighting configuration and the associated images.

BRIEF DESCRIPTION OF THE DRAWINGS

Implementations of the inventive concepts disclosed herein may be better understood when consideration is given to the following detailed description thereof. Such description makes reference to the included drawings, which are not necessarily to scale, and in which some features may be exaggerated and some features may be omitted or may be represented schematically in the interest of clarity. Like reference numerals in the drawings may represent and refer to the same or similar element, feature, or function. In the drawings.

DETAILED DESCRIPTION OF EXEMPLARY EMBODIMENTS

Figure 1A:
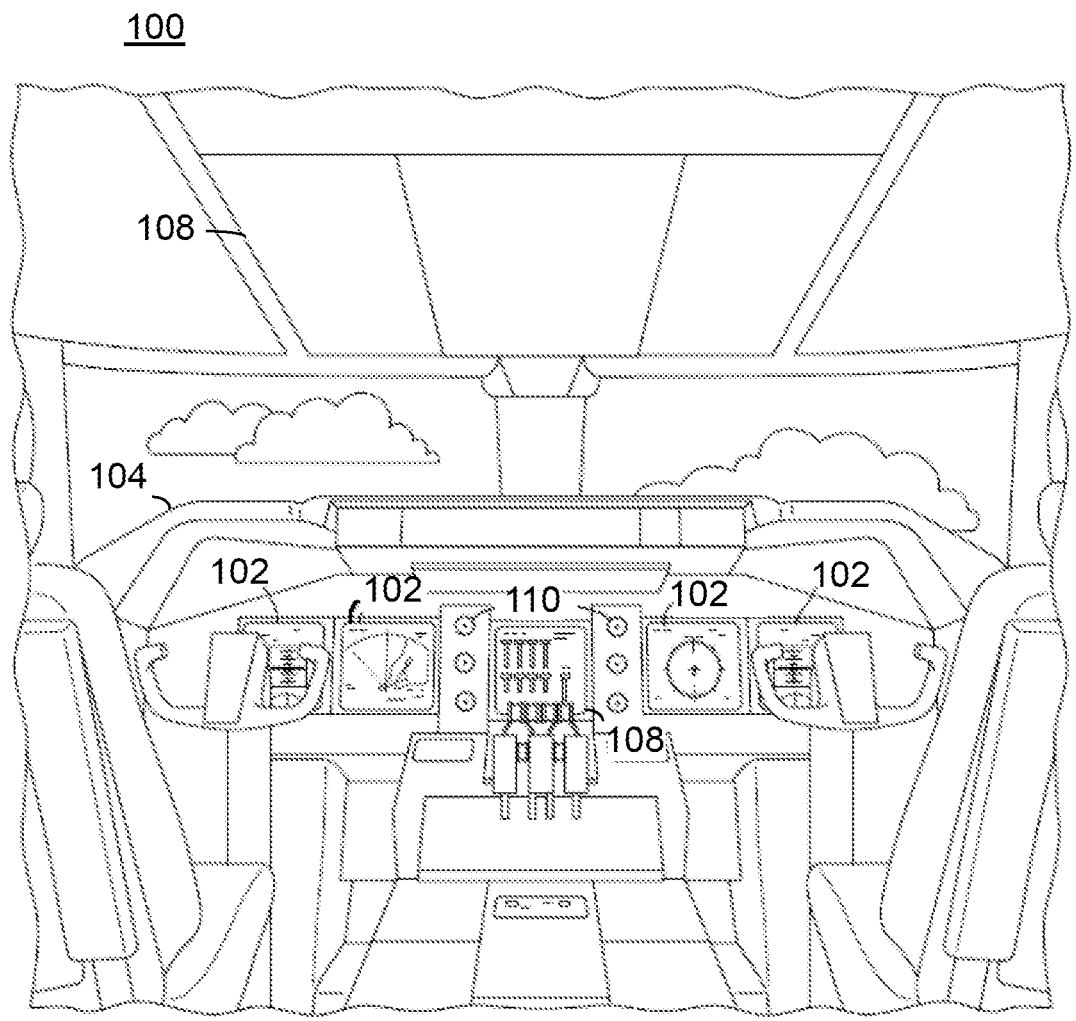
FIG. 1A depicts a perspective view of an aircraft system, in accordance with one or more embodiment of the present disclosure.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. In the following detailed description of embodiments of the instant inventive concepts, numerous specific details are set forth in order to provide a more thorough understanding of the inventive concepts. However, it will be apparent to one of ordinary skill in the art having the benefit of the instant disclosure that the inventive concepts disclosed herein may be practiced without these specific details. In other instances, well-known features may not be described in detail to avoid unnecessarily complicating the instant disclosure. The inventive concepts disclosed herein are capable of other embodiments or of being practiced or carried out in various ways. Also, it is to be understood that the phraseology and terminology employed herein is for the purpose of description and should not be regarded as limiting.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only, and should not be construed to limit the inventive concepts disclosed herein in any way unless expressly stated to the contrary.

Further, unless expressly stated to the contrary, "or" refers to an inclusive or and not to an exclusive "or". For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of embodiments of the instant inventive concepts. This is done merely for convenience and to give a general sense of the inventive concepts, and "a" and "an" are intended to include one or at least one and the singular also includes the plural unless it is obvious that it is meant otherwise.

Finally, as used herein any reference to "one embodiment," or "some embodiments" means that a particular element, feature, structure, or characteristic described in connection with the embodiment is included in at least one embodiment of the inventive concepts disclosed herein. The appearances of the phrase "in some embodiments" in various places in the specification are not necessarily all referring to the same embodiment, and embodiments of the inventive concepts disclosed may include one or more of the features expressly described or inherently present herein, or any combination or sub-combination of two or more such features, along with any other features which may not necessarily be expressly described or inherently present in the instant disclosure.

Lighting within the cockpit of an aircraft system may introduce artifacts into a video stream captured of eyes of an aircraft operator. The lighting may cause the eyes of the operator to autonomically respond due to a pupillary light reflex. For example, a brightness or a change in the lighting configuration of the cockpit may cause a pupil dilation or contraction based on how much light is received by the eyes. Such pupil response may introduce the artifacts. The lighting within a cockpit may be from a number of sources including internal light sources and external light sources. The internal light sources include images generated by the flight displays, glare shield lighting, panel lighting, and dome lighting. A lighting configuration for the internal light sources may be determined based on settings of various light control switches. Such light configuration may further impact a transmission of the lighting to and from the eyes of the aircraft operator.

Embodiments are generally directed to a method of simulating changes in ambient lighting within a cockpit to improve eye measurements. A three-dimensional replica of the layout of the cockpit is created in an environment. Lighting can then be systematically controlled, with associated images of the operator eyes being taken by a camera. The effects of the lighting change on pupil dilation are recorded as a baseline based on the captured images. Embodiments are also directed to compensating for lighting configurations of flight displays during flight, such as by using the recorded baseline. During flight, lighting information about flight displays and other cockpit elements are combined with the pupil dilation baselines to calibrate real-time images taken of the eyes of the aircraft operator. By calibrating the images with the lighting, noise caused by the pupil response to the changes in the flight display lighting may be compensated. These light compensated pupil metrics may then be used for various purposes, such as, but not limited to, determining aircraft operator fatigue with increased accuracy. The operator fatigue may thus be objectively determined using highly accurate pupillometry measurements in varying lighting conditions in real-time or near real-time.

Figure 1B:
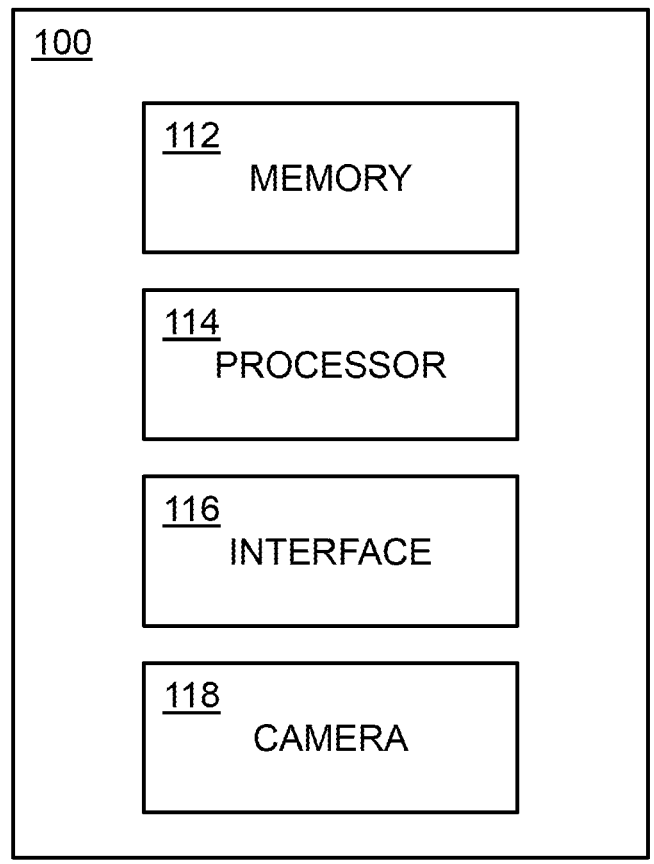
FIG. 1B depicts a simplified schematic view of an aircraft system, in accordance with one or more embodiments of the present disclosure.

Referring now to FIGS. 1A-1B, an aircraft system 100 is described, in accordance with one or more embodiments of the present disclosure. The aircraft system 100 may be embodied within a cockpit of an aircraft. The aircraft system 100 may further include various components disposed outside of the cockpit, such as, but not limited to processing elements housed in an integrated modular avionics (IMA) controller, or the like. The aircraft system 100 may include an aircraft operator (not depicted), such as a pilot, a co-pilot, or a second officer seated within the cockpit. The aircraft system 100 may also include one or more flight displays 102, glare shield 104, aircraft instruments 106, or dome lighting 108. A lighting configuration of the aircraft system 100 may be based on light output from the flight displays 102, glare shield 104, aircraft instruments 106, and dome lighting 108. The aircraft system 100 may further include one or more user interface elements 110. The user interface elements 110 may provide the operator with selective control of the lighting configuration, among other functions. The number and arrangement of the various elements within the aircraft system 100 may be based on the type of the aircraft. Thus, the configuration of FIG. 1 is not intended to be limiting but is merely provided for exemplary purposes.

The aircraft system 100 may include one or more flight displays 102. The flight displays 102 may be implemented using any of a variety of display technologies, including CRT, LCD, organic LED, dot matrix display, and others. The flight displays 102 may be configured to function to display various information known in the art. The flight displays 102 may be configured to function as one or more of a primary flight display (PFD) or a multifunction display (MFD). Such PFD and MFDs may be mounted in front of both a pilot and a copilot. The MFD may be mounted between the PFD of the pilot and the PFD of the copilot. Thus, the flight displays 102 may provide instrumentation for the operation of an aircraft. The images shown on the flight displays 102 may include monochrome or color display images (graphical representations) of various avionics data, such as, but not limited to, an indication of altitude of other aircraft, weather conditions, terrain, the altitude and/or location of such information relative to the aircraft, and so on. Such images may generate ambient lighting within the aircraft system 100. The flight displays 102 may be configured to function as, for example, a primary flight display (PFD) used to display altitude, airspeed, vertical speed, navigation and traffic collision avoidance system (TCAS) advisories; a crew alert system (CAS) configured to provide alerts to the flight crew; a multi-function display used to display navigation maps, weather radar, electronic charts, TCAS traffic, aircraft maintenance data and electronic checklists, manuals, and procedures; an engine indicating and crew-alerting system (EICAS) display used to display critical engine and system status data, and so on. Other types and functions of the flight displays 102 are contemplated and will be apparent to those skilled in the art.

The aircraft system 100 may include one or more glare shields 104. The glare shields 104 may be attached to some portion of the flight deck of the cockpit. The glare shield 104 may include various lighting. Such lighting may illuminate one or more of the flight displays 102 or the aircraft instruments 106.

The aircraft system 100 may include one or more aircraft instruments 106. The aircraft instruments 106 may include, but are not limited to, left, center, right, overhead, second officer, or other aircraft instruments. The aircraft instruments 106 may be implemented using any of a variety of technologies, including CRT, LCD, organic LED, dot matrix display, and others. It is further contemplated that the aircraft instruments 106 of the aircraft system 100 may include aircraft instruments (panels) which use analog indicators. In some instances, the aircraft instruments 106 may be backlit with one or more colors (e.g., red, blue-white, night vision compatible green, a color within the visible spectrum, etc.). The aircraft instruments 106 may indicate information associated with various flight instruments of the aircraft, such as, but not limited to, attitude, heading, vertical speed, air speed, altimeter, or turn. The aircraft instruments 106 may also indicate information associated with various engine instruments of the aircraft, such as, but not limited to, fuel quantity, oil quantity, oil pressure, oil temperature, tachometer, temperature, braking pressure, braking temperature, among others. The aircraft instruments 106 may also indicate information associated with various navigation instruments of the aircraft. Other types and functions of the aircraft instruments 106 are contemplated and will be apparent to those skilled in the art.

The aircraft system 100 may include one or more of the dome lighting 108. The dome lighting 108 may be a color of light, such as a white light. The dome lighting 108 may be turned-on during certain phases of flight, such as, but not limited to, prior-to and during taxiing of the aircraft. The dome lighting 108 may also be selectively turned-on, such as upon failure of flight instrument backlights.

Thus, the aircraft system 100 may include a number of internal light sources which may emit light. Such internal light sources may include the previously described flight displays 102, glare shields 104, aircraft instruments 106, and dome lighting 108. Other types of internal cockpit lighting are contemplated and will be apparent to those skilled in the art.

The internal light sources may further be selectively controlled. The selective control may include, but is not limited to, controlling which a brightness of the internal light sources by selectively controlling a power to the internal light sources (or similar means of brightness control). The aircraft system 100 may include one or more of the user interface elements 110 for providing the selective control of the internal light sources. The user interface elements 110 may include various buttons, toggles, switches, rockers, knobs, dimmers, touchscreen elements, and the like for controlling the internal lighting. For example, the user interface elements 110 may selectively control one or more of the flight displays 102, the glare shields 104, the aircraft instruments 106, or the dome lighting 108.

By the selective control of the internal light sources, the aircraft system 100 may include a number of lighting configurations. The lighting configuration may include which of the flight displays 102, glare shield 104, aircraft instruments 106, or dome lighting 108 are powered-on. The lighting configuration may also include a brightness setting (or similar) of the flight displays 102, glare shield 104, aircraft instruments 106, or dome lighting 108. The brightness setting may be based on the current setting of the user interface elements 110 or a state-of flight. The brightness setting may affect a number of photometric quantities associated with the flight displays 102, glare shield 104, aircraft instruments 106, or dome lighting 108. Such photometric quantities may include, but are not limited to, luminous energy, luminous power, luminous intensity, luminance, or illuminance.

In some embodiments, the lighting configuration may further include various display imagery generated on the flight displays 102. In this regard, the display imagery of the flight displays 102 may include the previously described images displayed on the PFD or MFD. Depending upon the state of flight, the display imagery may change between various colors and intensities, which may in turn cause an autonomic pupil response from the operator. For example, during an warning event, the display imagery may increase in brightness and may display various color symbology which may cause a autonomic pupil response.

In some embodiments, the lighting configuration may further include external lighting information. Such external lighting information may indicate a brightness of the sun due to positions of the aircraft relative to the sun, together with the time of day and various weather conditions. In some embodiments, the aircraft system 100 includes a photometric sensor to determine the external lighting information. In other embodiments, the aircraft system 100 receives the external lighting information from an avionics system (e.g., a weather radar or the like) of the aircraft.

Referring now in particular to FIG. 1B. The aircraft system 100 may further include one or more of a memory 112, processor(s) 114, network interface 116, and camera 118. During flight operations, the aircraft operator may gaze at various elements of the aircraft system 100, such as, but not limited to, the flight displays 102, the aircraft instruments 106, or out of a window. A pattern of the gaze may provide a biomarker of the aircraft operator. The biomarker may be indicative of a fatigue of the operator. The camera 118 may capture a video stream of the eye gazing at the various locations. The video stream may be provided to the processors 114 for image processing. The processors 114 may then perform various processor executable functions, such as, detecting an eye within frames of the video stream, correcting for the lighting configuration, and detecting operator fatigue.

The aircraft system 100 may include the memory 112. The memory 112 of the aircraft system 100 may include any storage medium known in the art. For example, the storage medium may include a non-transitory memory medium. For instance, the non-transitory memory medium may include, but is not limited to, a read-only memory (ROM), a random-access memory (RAM), a magnetic or optical memory device (e.g., disk), a solid-state drive and the like. It is further noted that memory may be housed in a common controller housing with the one or more processor(s). For example, the memory and the processor may be housed in an integrated modular avionics (IMA) controller, or the like. In an alternative embodiment, the memory may be located remotely with respect to the physical location of the processor. In another embodiment, the memory maintains program instructions for causing the processor(s) to carry out the various steps described through the present disclosure.

The aircraft system 100 may further include one or more processors 114. The processors 114 may include any processing unit known in the art. For example, the processors 114 may include a multi-core processor, a single-core processor, a reconfigurable logic device (e.g., FPGAs), a digital signal processor (DSP), a special purpose logic device (e.g., ASICs)), or other integrated formats. Those skilled in the art will recognize that aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software/and or firmware would be well within the skill of one skilled in the art in light of this disclosure. Such hardware, software, and/or firmware implementation may be a design choice based on various cost, efficiency, or other metrics. In this sense, the processor(s) may include any microprocessor-type device configured to execute software algorithms and/or instructions. In general, the term "processor" may be broadly defined to encompass any device having one or more processing elements, which execute program instructions from memory 112, from firmware, or by hardware implemented functions. It should be recognized that the steps described throughout the present disclosure, such as, but not limited to, the method 300, may be carried out by the processors 114.

The aircraft system 100 may further include a network interface 116. The network interface 116 may include any standard interface, such as, but not limited to, ARINC 429, ARINC-664, ethernet, AFDX, serial, CAN, TTP, Military Standard (MIL-STD) 1553, peripheral component interconnect (PCI) express, digital interfaces, analog interfaces, discrete interfaces, or the like. The network interface 116 may be configured to receive data, such as, but not limited to, the lighting configuration. The lighting configuration may be received from one or more of the flight displays 102, glare shield 104, aircraft instruments 106, dome lighting 108, or an photosensor indicative of external lighting.

The aircraft system 100 may further include the camera 118. The camera 118 may capture a video stream of the eye gazing at the various locations. The camera 118 may include any suitable camera, such as, but not limited to, a camera-based gaze sensor capturing the video stream of the eye. The camera 118 may be positioned and oriented to capture the eye of the operator during operation of the aircraft. The camera 118 may be disposed in a number of locations within the aircraft system 100, such as, but not limited to, within a head-mounted display or coupled to the flight deck of the cockpit. The camera 118 may also be communicatively coupled to the processors 114. For example, the camera 118 may be communicatively coupled to the processors 114 by way of the network interface 116. The camera 118 may thus provide the video stream the processors 114.

During flight, the processors 114 may receive information (e.g., by way of the network interface 116) regarding the lighting configuration. The processors 114 may further receive the video stream from the camera 118. The processors 114 may then analyze the video stream to determine a fatigue level of the operator. In some embodiments, the processor compensates for the lighting configuration when analyzing the video stream. The processor may compensate for the lighting configuration by a light compensation model. The light compensation model may be a pre-trained model which is stored in the memory 112. For example, the light compensation model may be trained as described further herein with regards to the method 200.

Figure 2:
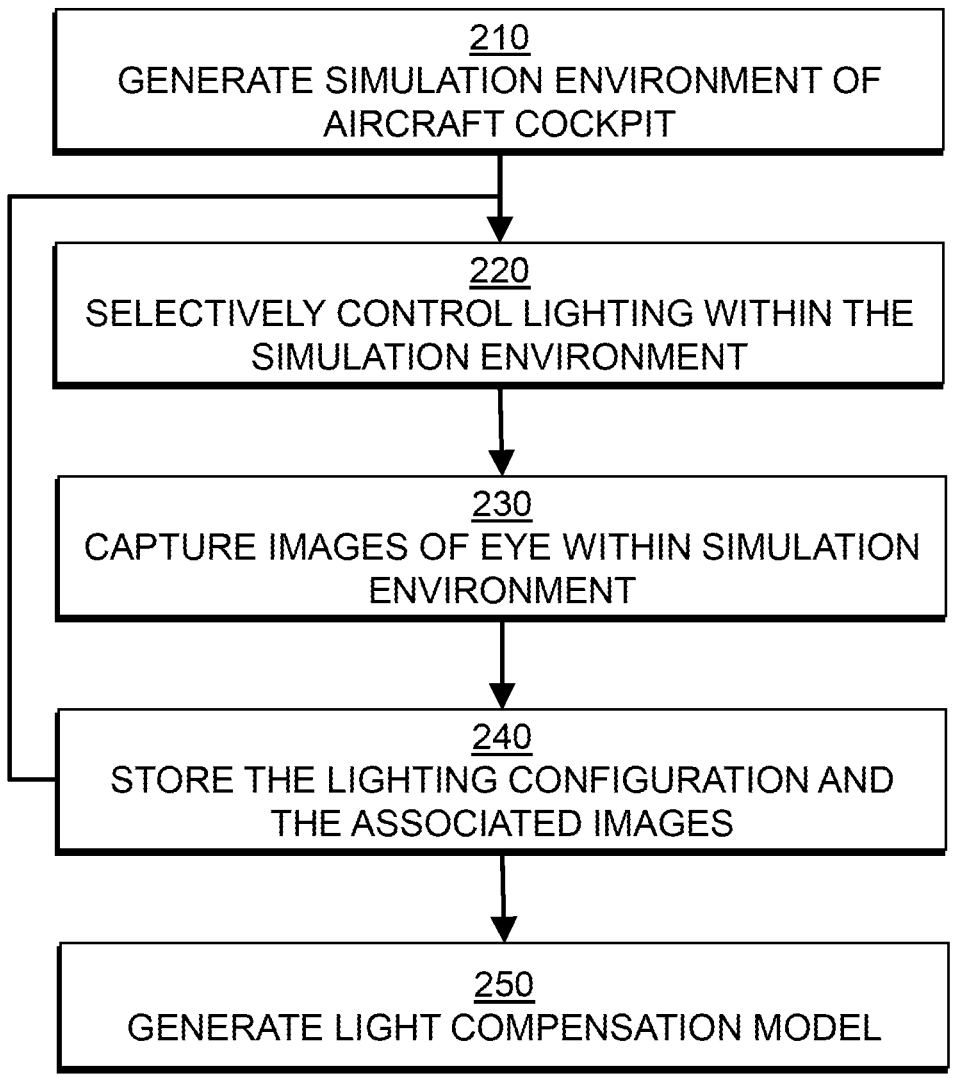
FIG. 2 depicts a flow diagram of a method for generating a light compensation model, in accordance with one or more embodiments of the present disclosure.

Referring now to FIG. 2, a method 200 of generating a light compensation model is described, in accordance with one or more embodiments of the present disclosure. The light compensation model generated by the method 200 may then be provided to the memory of the aircraft system 100, to compensate for the lighting configurations during flight.

In a step 210, a simulation environment is generated of a cockpit of an aircraft. The simulation environment includes various features of the cockpit, such as, but not limited to, flight displays, glare shield, aircraft instruments, or dome lighting, similar to those described with reference to the aircraft system 100. As may be understood, the number and layout of the flight displays, glare shield, aircraft instruments, and dome lighting in the simulation environment may be based on a type of the aircraft being simulated. In this regard, a number of such configurations may exist in the art. As may be understood, the layout of the cockpit may depend, at least in part, on the type of the aircraft. Similarly, recorded images of the pupils may be dependent upon the configurations.

In some embodiments, the simulation environment is a physical simulation environment. The physical simulation environment may be a full flight simulator (FSS) system. The full flight simulator may include physical copies of the flight displays, glare shield, aircraft instruments, or dome lighting, similar to those found in the same type of aircraft. The full flight simulator may further include a display (e.g., a collimated display) for displaying out-the-window imagery. The full flight simulator may or may not include axis motion control. The full flight simulator further includes one or more camera for capturing a video stream of a test operator within the environment.

In some embodiments, the simulation environment is a virtual simulation environment. The virtual simulation environment may be presented to the test operator by a head-mounted display, such as a virtual reality (VR) headset. The VR headset may include any VR headset known in the art. The VR headset may present a virtual representation of the cockpit, including virtual copies of the copies of the flight displays, glare shield, aircraft instruments, or dome lighting. The head-mounted display may further include one or more cameras for capturing a video stream of the test operator viewing the virtual representation.

In a step 220, lighting within the simulation environment is selectively controlled to a lighting configuration. The lighting configuration may be similar to the lighting configuration previously described in reference to the aircraft system 100. In this regard, the lighting configuration may include which of the flight displays, glare shield, aircraft instruments, or dome lighting are power-on together with a brightness setting for each of such lights that are turned on. The lighting configuration may further include the display images which are displayed on the flight displays. The lighting configuration may further include the out-the-window imagery (e.g., virtual sunlight, etc.) simulating the external lighting due to positions of the aircraft relative to the sun, together with the time of day and various weather conditions. Where the simulation environment is the physical simulation environment, the flight displays, glare shield, aircraft instruments, and dome lighting may be physically adjusted according to the lighting configuration. Where the simulation environment is the virtual simulation environment, the VR headset may generate display imagery representative of changes to the virtual flight displays, virtual glare shield, virtual aircraft instruments, and virtual dome lighting.

In a step 230, one or more images of the eye of the test operator are captured while the simulation environment is generating light according to the lighting configuration. The images correspond to light reflected from an eye of an operator viewing the lighting configuration of the simulation environment. The number of images captured may be sufficient to provide a representative quantity for the given lighting configuration. The images may include reactions of the eye of the test operator, which may serve as a baseline reaction to the lighting configuration with the cockpit. In particular, the images may represent a recording of the pupillary response of the operator to the lighting. Such pupil response may include, but is not limited to, changes in pupil diameter. The images may be captured in any suitable manner, such as, but not limited to a camera within the full flight simulator or the head-mounted display.

In a step 240, the lighting configuration and the associated images are stored in a memory. The steps 210 through 240 may then be repeated until a desired number of lighting configurations and images associated with the lighting configurations have been stored. For example, the steps 210 through 240 may be iteratively repeated for all possible lighting configurations of the cockpit. However, taking images for all possible lighting configurations may be prohibitive, due to the time constraints associated with the exponential nature of the number of lights and the possible light settings. By way of another example, the steps 210 through 240 may be iteratively repeated for a subset of all possible lighting configurations of the cockpit. The subset may be selected using any of a number of statistical methods known by one skilled in the art. For instance, the subset may be selected by a dimension reduction method, or similar.

Furthermore, the steps 210 through 240 may be repeated for a selected number of test operators. Furthermore, the steps 210 through 240 may be repeated for a selected type of cockpit.

In a step 250, a light compensation model is generated based on the lighting configuration and the associated images stored in the memory. The light compensation model may be generated by a number of machine learning model architectures. The architecture used to generate the light compensation model may include, but is not limited to, a classification model. For example, the classification model may include a random forest, a naïve bayes, a support vector machine (SVM), or an XGBoost model. Subsequent to generating the light compensation model, the light compensation model may be provided to the aircraft system 100 and stored in the memory 112. Generally, the method 200 may be performed prior to flight operations, such that the light compensation model may be considered a pre-trained model.

Figure 3:
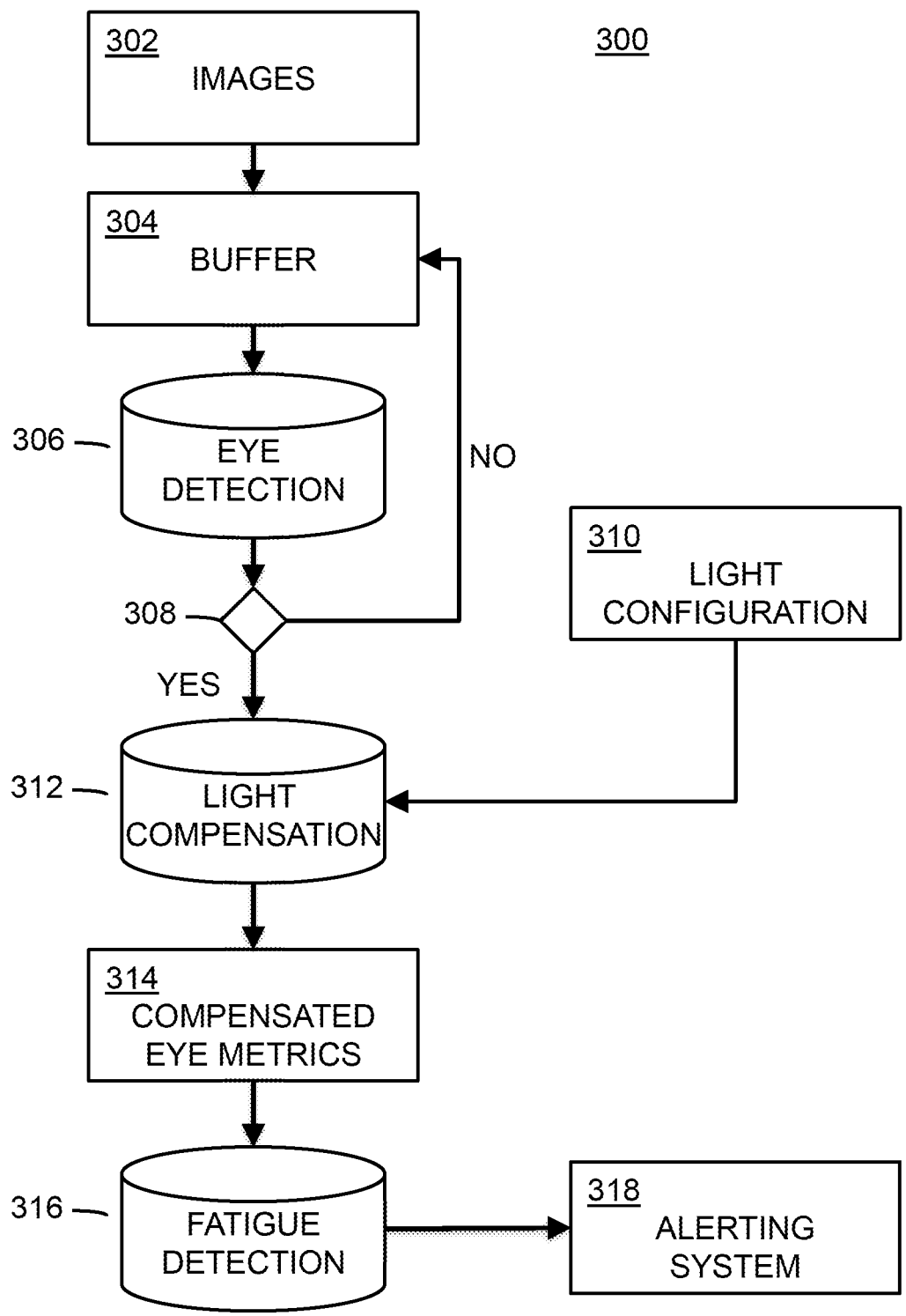
FIG. 3 depicts a flow diagram of a method for compensating for pupillary light reflex of an operator eye due to a lighting configuration of an aircraft system, in accordance with one or more embodiments of the present disclosure.

Referring now to FIG. 3, a method 300 is described, in accordance with one or more embodiments of the present disclosure. The embodiments and the enabling technology described previously herein in the context of the aircraft system 100 and the method 200 should be interpreted to extend to the method 300. It is further recognized, however, that the method 300 is not limited to the aircraft system 100 and the method 200. Similarly, the embodiments and enabling technology of the method 300 should be interpreted to be implemented by the processors of the aircraft system 100.

In a step 302, one or more images are received. The images may be received from a camera within an aircraft cockpit (e.g., camera 118). The images may represent light reflected from the eye of an operator occupying the cockpit. The camera may include any camera known in the art, such as, but not limited to, an RGB camera.

In a step 304, the images are stored in an image buffer. The image buffer may include any data buffer known in the art. The images may be stored in physical memory in a temporary manner as the images are processed by an eye detection model. For example, the images may be stored on a memory of the aircraft system 100 (e.g., memory 112). In some instances, the image buffer may be configured as a first-in, first-out (FIFO) buffer. It is contemplated that various modifications to the storage of the images may be made by one of ordinary skill in the art.

In a step 306, an eye detection model is applied to one of the images stored in the image buffer. The eye detection model may be a pre-trained model, such as, but not limited to, a pre-trained deep learning model. The eye detection model may generate various eye metrics. The eye metrics may include a position of the eye within the image, blink events, or various landmarks or locations associated with eyelid, pupil, iris of the eyes operator. However, such eye metrics may not be compensated for the pupillary response to the aircraft lighting.

In a step 308, a check is made to determine whether there is an eye detected within the image by the eye detection model. Upon no eye being detected, the method 300 may retrieve the next image from the buffer and apply the eye detection model to the next image. Upon an eye being detected, the method may proceed with compensating for the lighting configuration of the aircraft.

In a step 310, a lighting configuration for light sources of an aircraft is received. The lighting configuration information may be based on the lighting configuration of the various internal light sources of the aircraft when the images of the aircraft operator where taken. The lighting configuration may indicate various information, such as, but not limited to, a brightness of one or more flight displays, glare shields, aircraft instruments, or dome lighting. The lighting may further indicate the images displayed on the flight display. The lighting configuration may further indicate external lighting information, such as, but not limited to, a time of day, a weather condition, or a position of the sun.

Such external light data may be received by way of various avionics systems onboard the aircraft. In some instances, the external lighting information may be generated by and received from a photosensor.

Although the step 302 and the step 310 are depicted as separate steps in the method 300, this is not intended to be a limitation on the present disclosure. In this regard, the light configuration may be received at any point prior to the step 312 of light compensation. In some instances, the lighting configuration may be recorded with a given frequency. The frequency of recording the lighting configuration may be less than, equal to, or greater than the frequency at which images are recorded. Typically, the frequency of recording the lighting configuration may be lower than the frequency of recording the images, due to the relatively infrequent nature of lighting configuration changes as compared to the frame rate at which the images may be recorded. However, where the lighting configuration includes the display imagery from the flight displays, the lighting configuration may be recorded based on a refresh rate of the flight displays, such that the lighting configuration may be recorded more frequently than the images recorded by the camera.

In a step 312, a light compensation model is applied for each of the images. The light compensation model may use the position of the eye determined in the step 308 together with the lighting configuration received in the step 310. The light compensation model may then compensate for an autonomic pupil response (e.g., pupil dilation, saccadic movement, etc.) of the eye due to the lighting. The light compensation model may then output various metrics (see step 314). Although not depicted, multiple of the light compensation models may be available. The light compensation model may be selected based on various data regarding the cockpit of the aircraft, such as, but not limited to, the type of aircraft, the layout of the cockpit, or the condition of the flight. Each of the light compensation models may be generated in a manner, such as, but not limited to, by the method 200.

In a step 314, one or more metrics are determined from the light compensation model. The metrics may include eye metrics which have been compensated, corrected, or otherwise adjusted based on the lighting of the aircraft (e.g., light compensated eye metrics). The eye metrics may include, but are not limited to, gaze direction, pupil diameter, eyelid tracking, blink rate, blink duration, or eye movements. The eye movements may include one or more of smooth pursuit movements, vergence movements, and saccadic movements. Such saccadic movements are of particular interest in the context of detecting aircraft operator fatigue. The saccadic movements may include various parameters, such as, but not limited, saccade velocity (linear or angular) or distance. It further is contemplated that additional eye metrics in the field of pupillometry may suitable for such light compensation.

By calibrating the video stream with the light configuration, a noise associated with autonomic pupil response to the cockpit lighting may be reduced. Thus, the step 314 may provide a real-time or near-real time means of increasing the accuracy of the pupillometry measurements in varying aircraft lighting conditions. This may be particularly beneficial in improving an accuracy in fatigue level estimation of the operator.

In a step 316, a fatigue level of the aircraft operator is estimated. The fatigue level may be estimated by applying a fatigue detection model to the eye metrics determined in the step 314. The fatigue detection model may use one or more of the pupil diameter, eyelid tracking, blink rate, blink duration, or eye movements to estimate the fatigue level. Similarly, the fatigue detection model may be applied to the eye metrics from a set of images to which the eye detection model and the light compensation model have been applied. The fatigue level may thus provide a relatively object measure of fatigue for the aircraft operator in real time or near-real time.

In a step 318, the fatigue level may be provided to an alerting system. The alerting system may compare the fatigue level to one or more fatigue level thresholds. In the event that the fatigue level exceeds the fatigue level threshold, the alerting system may cause an alert to be displayed to the aircraft operator (e.g., by a flight display, auditory cue, etc.) or sent to a ground crew.

Referring generally again to FIGS. 1A-3.

All of the methods described herein may include storing results of one or more steps of the method embodiments in memory. The results may include any of the results described herein and may be stored in any manner known in the art. The memory may include any memory described herein or any other suitable storage medium known in the art. After the results have been stored, the results can be accessed in the memory and used by any of the method or system embodiments described herein, formatted for display to a user, used by another software module, method, or system, and the like. Furthermore, the results may be stored "permanently," "semi-permanently," temporarily," or for some period of time. For example, the memory may be random access memory (RAM), and the results may not necessarily persist indefinitely in the memory. It is further contemplated that each of the embodiments of the method described above may include any other step(s) of any other method(s) described herein. In addition, each of the embodiments of the method described above may be performed by any of the systems described herein.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A computer-implemented method comprising:
 receiving a plurality of images and a lighting configuration, the plurality of images taken by a camera during operation of an aircraft, the plurality of images corresponding to light reflected from an eye of an operator occupying a cockpit of the aircraft, wherein the light reflected from the eye is based on the lighting configuration, the lighting configuration corresponding to a plurality of flight displays and one or more aircraft instruments, wherein the lighting configuration includes a brightness setting of the plurality of flight displays and the one or more aircraft instruments;
 determining a position of the eye for each of the plurality of images by applying an eye detection model to each of the plurality of images; and generating one or more light-compensated pupil metrics for each of the plurality of images by applying a light compensation model to each of the plurality of images, the light compensation model using the position of the eye and the lighting configuration to correct for a pupillary light reflex of the eye, wherein the light-compensated pupil metrics include a saccadic movement and a pupil diameter.

2. The computer-implemented method of claim 1, further comprising:
estimating a fatigue level of the operator based on the one or more light-compensated metrics;
determining the fatigue level exceeds a threshold; and
causing at least one of the plurality of flight displays to display an alert in response to determining the fatigue level exceeds the threshold.

3. The computer-implemented method of claim 1, wherein the light compensation model is a pre-trained machine learning model.

4. The computer-implemented method of claim 3, wherein the pre-trained machine learning model is one of a random forest, naïve bayes, support vector machine, or XGBoost.

5. The computer-implemented method of claim 1, wherein the light-compensated pupil metrics include an eyelid tracking, a blink rate, the saccadic movement, and the pupil diameter.

6. The computer-implemented method of claim 1, further comprising receiving external light data, wherein the light compensation model further uses the external light data to correct for the pupillary light reflex of the eye.

7. The computer-implemented method of claim 6, wherein the external light data includes at least one of a time, a weather condition, or a signal from a light sensor.

8. An aircraft system comprising:
a plurality of flight displays within a cockpit of an aircraft, the plurality of flight displays each generating one or more display images during operation of the aircraft;
one or more aircraft instruments within the cockpit;
a camera positioned and oriented within the cockpit such that the camera is configured to capture a plurality of images, the plurality of images taken by the camera during the operation of the aircraft, the plurality of images corresponding to a light reflected from an eye of an operator occupying the cockpit of the aircraft, wherein the light reflected from the eye is based on a lighting configuration of the plurality of flight displays and the one or more aircraft instruments, wherein the lighting configuration includes a brightness setting of the plurality of flight displays and the one or more aircraft instruments;
a processor configured to execute program instructions maintained on a memory, the program instructions causing the processor to:
receive the plurality of images and the lighting configuration;
determine a position of the eye for each of the plurality of images by applying an eye detection model to each of the plurality of images; and
generate one or more light-compensated pupil metrics for each of the plurality of images by applying a light compensation model to each of the plurality of images, the light compensation model using the position of the eye and the lighting configuration to correct for a pupillary light reflex of the eye, wherein the light-compensated pupil metrics include a saccadic movement and a pupil diameter.

9. The aircraft system of claim 8, wherein the plurality of flight displays include at least two primary flight displays and at least one multi-function display; wherein the at least one multi-function display is mounted between the at least two primary flight displays; wherein the lighting configuration includes a lighting configuration for the at least two primary flight displays and the at least one multi-function display, wherein the light compensation model uses the lighting configuration for the at least two primary flight displays and the at least one multi-function display to generate the light-compensated pupil metric.

10. The aircraft system of claim 8, wherein the light compensation model is pre-trained in a simulation environment.

11. The aircraft system of claim 8, wherein the processor is further configured to store the plurality of images and the lighting configurations in a buffer of the memory; wherein the processor is further configured to retrieve the plurality of images and the lighting configurations from the buffer for determining the position of the eye and generating the light-compensated pupil metrics.

12. The aircraft system of claim 11, wherein upon failing to detect a position of the eye for at least one of the plurality of images, the processor is further configured to retrieve a subsequent image stored in the buffer.

13. The aircraft system of claim 8, wherein the lighting configuration further includes display images from the plurality of flight displays, wherein the light compensation model uses the display images to generate the light-compensated pupil metrics.

14. The aircraft system of claim 13, wherein the plurality of display images includes color display images, wherein the camera is a color-camera.

15. The aircraft system of claim 14, wherein the camera is one of mounted to a flight deck of the cockpit or a component of a head-mounted display.

* * * * *